United States Patent [19]

Morisawa et al.

[11] 4,259,350

[45] Mar. 31, 1981

[54] IODOPROPARGYL DERIVATIVES, THEIR USE AND PREPARATION

[75] Inventors: Yasuhiro Morisawa; Kiyoshi Konishi; Mitsuru Kataoka, all of Hiromachi, Japan

[73] Assignee: Sankyo Company Limited, Tokyo, Japan

[21] Appl. No.: 20,165

[22] Filed: Mar. 13, 1979

[30] Foreign Application Priority Data

Mar. 15, 1978 [JP] Japan ................................. 53-29546
Dec. 15, 1978 [JP] Japan ................................. 53-154673

[51] Int. Cl.³ .................... A01N 37/10; A01N 37/34; A01N 43/02; A01N 43/40
[52] U.S. Cl. .................................... 424/308; 424/266; 424/275; 424/285; 424/304; 424/309; 549/71; 260/29.6 MN; 260/29.6 ME; 260/29.6 R; 260/347.5; 260/410.9 N; 260/456 P; 260/456 R; 260/463; 546/301; 546/302; 546/318; 546/326; 560/1; 560/61; 560/104; 560/105; 560/111; 560/122; 560/123; 560/223; 560/229; 560/262
[58] Field of Search ................ 560/111; 424/308, 304, 424/309

[56] References Cited

U.S. PATENT DOCUMENTS

| | | | |
|---|---|---|---|
| 3,080,405 | 3/1963 | Larsea et al. ........................ | 560/111 |
| 3,256,305 | 6/1966 | Gijzen ................................. | 560/111 |
| 3,660,499 | 5/1972 | Kobayoshi et al. ................. | 424/258 |
| 3,780,089 | 12/1973 | Widdig et al. ....................... | 424/309 |
| 3,879,445 | 4/1975 | Gray et al. .......................... | 560/111 |
| 4,158,655 | 6/1979 | Brady .................................. | 560/111 |

OTHER PUBLICATIONS

Seki et al., English–Language Translation of Japanese Pat. No. 41-19077.
Sladkov et al.; C.A. vol. 63, (1968), 1718g.
Seki et al., C.A. vol. 68, (1968), 68693n.

Primary Examiner—Allen J. Robinson
Attorney, Agent, or Firm—Frishauf, Holtz, Goodman & Woodward

[57] ABSTRACT

Iodopropargyl derivatives of formula:

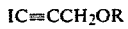

$IC{\equiv}CCH_2OR$

[wherein R represents an alkanoyl group (which may be unsubstituted or have one or more halogen, cyano, substituted or unsubstituted α-phenoxy or phenyl substituents) an alkenoyl group (optionally phenyl-substituted), a substituted or unsubstitutd alkoxycarbonyl group, a cycloalkanoyl group, a substituted or unsubstituted benzoyl group, a substituted or unsubstituted phenoxycarbonyl group, a substituted or unsubstituted benzyloxycarbonyl group, a heterocyclic carbonyl group, an alkylsulphonyl group, a substituted or unsubstituted benzenesulphonyl group, a naphthyloxycarbonyl group, an iodopropargyloxycarbonyl group, a substituted or unsubstituted cycloalkoxycarbonyl group, a heterocyclic methoxycarbonyl group, a 3-pyridyloxycarbonyl group (which may be unsubstituted or have one or more halogen substituents) or an alkenyloxycarbonyl group] are, except where R represents an acetyl or an unsubstituted benzoyl group, new compounds and are useful for the preservation of a variety or organic materials, including the protection of these materials against fungal or insect attack. The derivatives may be prepared by reacting 3-hydroxy-1-iodo-1-propyne with a compound of formula RX (in which R is as defined above and X represents a halogen atom) or, where R in the desired compound contains an oxycarbonyl group, reacting the 3-hydroxy-1-iodo-1-propyne with phosgene and then reacting the product with an appropriate hydroxy-containing compound.

17 Claims, No Drawings

IODOPROPARGYL DERIVATIVES, THEIR USE AND PREPARATION

BACKGROUND OF THE INVENTION

Most organic materials are susceptible, to some degree, to attack by a variety of natural pests, including fungus and insects. Susceptible materials include building materials (such as wood) and industrial materials (such as wet pulps, papers, mats, fibres, leathers, adhesives, paints, synthetic resins and, again, wood) the growth of undesirable fungi on these materials can lead not only to contamination but also to structural damage. In the past, reasonably effective control of fungi on such materials has been achieved by the application to these materials of a variety of anti-fungal compounds. The compounds most commonly employed for this purpose are organic compounds of heavy metals (e.g. compounds of lead or tin, particularly tributyltin oxide) or chlorinated phenols (such as pentachlorophenol). However, these substances are very toxic to humans and other animals and thus not only are they dangerous to handle during application, but they may also give rise to danger during use of the material treated with them. Furthermore, environmental pollution may occur if inadequate safety precautions are taken during treatment of organic materials with these anti-fungal agents or during the use or destruction (e.g. by incineration) of the materials treated. Accordingly, although these anti-fungal agents have proven of great value in the past, it is anticipated that their future use will be restricted or even banned.

However, the world's diminishing resources make it ever more vital that materials should be adequately preserved. For example, wood preservation has become of increasing importance in recent years due to increasing world demands upon dwindling forest resources and because of the introduction of new building processes (e.g. the prefabricatd frame process) and high temperature and humidity conditions in many parts of the world. This demand for preservatives for wood and other organic materials has not been met completely by preservatives of the chlorophenol, organotin or inorganic adhesive types, since they not only (as explained above) may be poisonous, but they may be inadequately effective, have an offensive smell and contaminate the material being treated, which makes it difficult to handle the material easily and safely. There is, therefore, a strong demand for a new anti-fungal and preservative agent which is more effective, easier to handle and safer.

Japanese patent application (examined) No. 19077/66 discloses a compound of general formula $IC{\equiv}C.CH_2OR^1$ (in which R' represents a phenyl or benzyl group which is unsubstituted or has one or more substituents, the substituents being on the aromatic nucleus and selected from halogen atoms, lower alkyl groups, nitro groups, carbamoyl groups, carboxyl groups and carboalkoxy groups); these compounds have been proposed for use as industrial anti-fungal agents.

Similar iodopropargyl derivatives are disclosed in Japanese patent application (examined) No. 33182/74, (which corresponds to U.S. Pat. No. 3,660,499) these iodopropargyl derivatives being of formula $ArOCH_2OCH_2C{\equiv}CI$ (in which Ar represents a phenyl group, a naphthyl group or a quinolyl group which are unsubstituted or have an alkyl, halogen or nitro substituent). These compounds have been suggested as fungicides.

Similar 1-iodo-alkyne derivatives are disclosed in Japanese patent application (unexamined) No. 31036/75 (which corresponds to U.S. Pat. No. 3,780,089) and suggested for use as fungicides.

3-Benzoyloxy-1-iodo-1-propyne is disclosed in Chemical Abstracts 63 1718 g (1965); however, no potential use or activity is described for this compound. Also, 1-acetoxy-1-iodo-1-propyne is disclosed in Chemical Abstracts 72, 3049 v; however, only its phytological activity, especially chemical pruning activity is disclosed.

After thorough study of a wide variety of compounds, we have now found that 3-benzoyloxy-1-iodo-1-propyne and 3-acetoxy-1-iodo-1-propyne and a closely related group of novel compounds have excellent anti-fungal activity and, moreover, have preservative and anti-insect (particularly termiticidal) activity.

BRIEF SUMMARY OF INVENTION

It is, therefore, an object of the invention to provide a series of novel iodopropargyl derivatives which are valuable antifungal, preservative and termiticidal agents.

It is a further object of the invention to provide an antifungal, preservative and termiticidal composition containing one or more iodopropargyl derivatives as the active agent.

It is a still further object of the invention to provide a method of preserving organic materials (particularly wood, leather and paper) against fungal or insect, particularly termite, attack by applying to or incorporating into the material an iodopropargyl derivative.

The novel iodopropargyl derivatives of the present invention are those compounds of general formula (I):

$$IC{\equiv}C.CH_2.OR \qquad (I)$$

in which:

R represents an alkanoyl group having at least 3 carbon atoms, an alkenoyl group, a halogenated alkanoyl group, a cyanoacetyl group, an α-phenoxyalkanoyl group, a substituted α-phenoxyalkanoyl group, a phenylalkanoyl group, a cinnamoyl group, a substituted cinnamoyl group, an alkoxycarbonyl group, a substituted alkoxycarbonyl group, a cycloalkanoyl group, a substituted benzoyl group, a phenoxycarbonyl group, a substituted phenoxycarbonyl group, a benzyloxycarbonyl group, a substituted benzyloxycarbonyl group, a heterocyclic carbonyl group, an alkylsulphonyl group, a benzenesulphonyl group, a substituted benzenesulphonyl group, a naphthyloxycarbonyl group, an iodopropargyloxycarbonyl group, a cycloalkoxycarbonyl group, a substituted cycloalkoxycarbonyl group, a heterocyclic methoxycarbonyl group, a 3-pyridyloxycarbonyl group, a halo-substituted 3-pyridyloxycarbonyl group or an alkenyloxycarbonyl group.

The invention also provides a method of protecting a degradable organic material from fungal or insect attack, which comprises applying to or admixing with said material an iodopropargyl derivative of general formula (Ia):

$$IC{\equiv}CCH_2OR^1 \qquad (Ia)$$

wherein:

$R^1$ represents any one of the groups defined for R or an acetyl group or a benzoyl group.

DETAILED DESCRIPTION OF INVENTION

In the above definition of the groups R and $R^1$, where a group is optionally substituted, the substituents are preferably in the cycloalkyl or aromatic ring system, where appropriate, and are preferably selected from: halogen atoms (especially chlorine, bromine and iodine); cyano groups; nitro groups; lower alkyl groups (especially methyl, ethyl, propyl, isopropyl, butyl, isobutyl and t-butyl); lower alkanoyl groups (especially acetyl); lower alkoxy groups (especially methoxy, ethoxy, propoxy, isopropoxy, butoxy, isobutoxy and t-butoxy); and lower alkyl or lower alkoxy groups substituted by any of the above substituents.

In the compounds of formula (I) and (Ia), when R or $R^1$ represents an alkanoyl group, this may be a straight or branched chain group and preferably has from 2 to 18 (3 to 18 in the case of $R^1$) carbon atoms. Examples of such groups include the acetyl, propionyl, butyryl, isobutyryl, pivaloyl, valeryl, isovaleryl, 2-methylbutyryl, hexanoyl, 2-methylvaleryl, 2-ethylbutyryl, heptanoyl, octanoyl, 2-ethylhexanoyl, nonanoyl, decanoyl, undecanoyl, lauryl, myristoyl, palmitoyl, stearoyl or isostearoyl groups.

Where R or $R^1$ represents an alkenoyl group, this may be a straight or branched chain group and preferably has from 3 to 18 carbon atoms. Examples include the acryloyl, methacryloyl, crotonoyl, butenoyl, sorboyl, oleoyl, 10-undecenoyl and linolyl groups.

Where R or $R^1$ represents a halogenated alkanoyl group, it may be straight or branched chain and preferably has from 2 to 12 carbon atoms. Preferred halogen substituents are chlorine or bromine and the group will normally have from 1 to 3 such substituents. Examples of such groups include the bromoacetyl, chloroacetyl, dichloroacetyl, trichloroacetyl, 2-bromopropionyl, 3-bromopropionyl, 2-chloropropionyl, 3-chloropropionyl, 2-bromobutyryl, 4-chlorobutyryl, 2-chlorobutyryl, 3-chlorobutyryl, 2-bromoisobutyryl, 2-bromovaleryl, 2-bromoisovaleryl, 2-bromohexanoyl, 2-bromooctanoyl and 11-bromoundecanoyl groups.

Where R or $R^1$ represents an α-phenoxyalkanoyl group, this may be unsubstituted or have one or more substituents. Where the group is substituted, the substituents are preferably on the phenyl moiety and are preferably 1 or 2 halogen atoms. The alkanoyl moiety preferably has from 2 to 4 carbon atoms. Examples of such groups include the phenoxyacetyl, 2-phenoxypropionyl, 2-phenoxybutyryl, o-chlorophenoxyacetyl, m-chlorophenoxyacetyl, p-chlorophenoxyacetyl, 2,4-dichlorophenoxyacetyl, o-bromophenoxyacetyl and p-bromophenoxyacetyl groups.

Where R or $R^1$ represents a phenylalkanoyl group, this is preferably a phenylacetyl or β-phenylpropionyl group. Where R or $R^1$ represents a cinnamoyl group, this may optionally have one or more substituents, preferably selected from halogen atoms, methoxy groups, methyl groups or nitro groups. Examples include the cinnamoyl group itself and the m-bromocinnamoyl, p-chlorocinnamoyl, -methoxycinnamoyl, p-methylcinnamoyl and o-nitrocinnamoyl groups.

When R or $R^1$ represents an alkoxycarbonyl group, this may be a straight or branched chain group and preferably has from 2 to 13 carbon atoms. Examples of such groups include the methoxycarbonyl, ethoxycarbonyl, n-propoxycarbonyl, isopropoxycarbonyl, n-butoxycarbonyl, isobutoxycarbonyl, sec-butoxycarbonyl, n-pentyloxycarbonyl, isopentyloxycarbonyl, n-hexyloxycarbonyl, sec-hexyloxycarbonyl, 2-methylpentyloxycarbonyl, 4-methyl-2-pentyloxycarbonyl, n-heptyloxycarbonyl, n-octyloxycarbonyl, 2-ethylhexyloxycarbonyl, n-nonyloxycarbonyl, 3,5,5-trimethylhexyloxycarbonyl, n-decyloxycarbonyl and n-dodecyloxycarbonyl groups.

Where R or $R^1$ represents a cycloalkanoyl group, this will normally have a 4, 5 or 6 membered ring and is preferably cyclobutanecarbonyl, cyclopentanecarbonyl or cyclohexanecarbonyl.

$R^1$ may represent a benzoyl group and both R and $R^1$ may represent a substituted benzoyl group. Where the group is substituted, it preferably has one or two substituents and these are preferably halogen atoms, methyl groups, methoxy groups, cyano groups or nitro groups. Where there are two substituents, the substituents may be the same or different. Examples of such groups are benzoyl itself and the o-chlorobenzoyl, m-chlorobenzoyl, p-chlorobenzoyl, o-bromobenzoyl, m-bromobenzoyl, p-bromobenzoyl, m-fluorobenzoyl, p-fluorobenzoyl, o-iodobenzoyl, p-iodobenzoyl, 2,4-dichlorobenzoyl, 3,4-dichlorobenzoyl, 3,5-dichlorobenzoyl, o-toluoyl, m-toluoyl, p-toluoyl, 2,4-dimethylbenzoyl, 3,4-dimethylbenzoyl, o-methoxybenzoyl, m-methoxybenzoyl, p-methoxybenzoyl, 2,4-dimethoxybenzoyl, 3,4-dimethoxybenzoyl, m-cyanobenzoyl, p-cyanobenzoyl, m-nitrobenzoyl, p-nitrobenzoyl, 4-chloro-2-methoxybenzoyl, 2-methyl-3-nitrobenzoyl, 2-methyl-4-nitrobenzoyl and 4-methyl-3-nitrobenzoyl groups.

When R or $R^1$ represents a heterocyclic carbonyl group, the heterocyclic system is preferably one containing one or more nitrogen, oxygen or sulphur atoms, particularly a pyridyl, thenyl or furyl group. Examples of suitable heterocyclic carbonyl groups include the nicotinoyl, isonicotinoyl, 2-pyridinecarbonyl, 2-thenoyl and 2-furoyl groups.

Where R or $R^1$ represents an alkylsulphonyl group, the alkyl is preferably a straight-chain group and it preferably has from 3 to 8 carbon atoms. Examples of suitable groups include the propanesulphonyl, butanesulphonyl, hexanesulphonyl and octanesulphonyl groups.

Where R or $R^1$ represents a benzenesulphonyl group, it may be substituted or unsubstituted and there are preferably provided one or two substituents, which may be the same or different and are preferably halogen atoms, methyl groups or methoxy groups. Examples of suitable benzenesulphonyl groups include benzenesulphonyl itself, p-chlorobenzenesulphonyl, p-bromobenzenesulphonyl, p-fluorobenzenesulphonyl, 2,5-dichlorobenzenesulphonyl, p-toluenesulphonyl and p-methoxybenzenesulphonyl groups.

When R or $R^1$ represents a substituted phenoxycarbonyl group, it preferably has from 1 to 3 substituents, which may be the same or different, and which are preferably halogen atoms, straight or branched chain alkyl groups (preferably having from 1 to 4 carbon atoms), methoxy groups, nitro groups or acetyl groups. Examples include o-bromophenoxycarbonyl, m-bromophenoxycarbonyl, p-bromophenoxycarbonyl, o-chlorophenoxycarbonyl, m-chlorophenoxycarbonyl, p-chlorophenoxycarbonyl, o-fluorophenoxycarbonyl, m-fluorophenoxycarbonyl, p-fluorophenoxycarbonyl, 2,3-dichlorophenoxycarbonyl, 2,4-dichlorophenoxycarbonyl, 2,5-dichlorophenoxycarbonyl, 2,6-dichlorophenoxycarbonyl, 3,4-dichlorophenoxycarbonyl, 3,5-dichlorophenoxycarbonyl, 2,3,5-trichlorophenoxycarbonyl, 2,4,5-trichlorophenoxycarbonyl, 2,4,6-trichlorophenoxycarbonyl, o-methyl-phenoxycarbonyl, m-methylphenoxycarbonyl, p-methylphenoxycarbonyl, 2,3-dimethylphenoxycarbonyl, 2,4-dimethylphenoxycarbonyl, 2,5-dimethylphenoxycarbonyl, 2,6-dimethylphenoxycarbonyl, 3,4-dimethylphenoxycarbonyl, 2,3,5-trimethylphenoxycarbonyl, o-ethylphenoxycarbonyl, m-ethylphenoxycarbonyl, p-ethylphenoxycarbonyl, o-propylphenoxycarbonyl, p-propylphenoxycarbonyl, 4-sec-butylphenoxycarbonyl, 4-t-butylphenoxycarbonyl, o-methoxyphenoxycarbonyl, m-methoxyphenoxycarbonyl, p-methoxyphenoxycarbonyl, 4-chloro-2-methylphenoxycarbonyl, 4-chloro-3-methylphenoxycarbonyl, o-nitrophenoxycarbonyl, m-nitrophenoxycarbonyl, p-nitrophenoxycarbonyl, 2,4-dinitrophenoxycarbonyl, o-acetylphenoxycarbonyl, m-acetylphenoxycarbonyl, p-acetylphenoxycarbonyl, 3-methyl-4-nitrophenoxycarbonyl, or 4-methyl-2-nitrophenoxycarbonyl groups.

Where R or $R^1$ represents a naphthyloxycarbonyl group, this may be a 1- or 2-naphthyloxycarbonyl group.

Where R or $R^1$ represents a substituted benzyloxycarbonyl group, there are preferably 1 or 2 substituents, which may be the same or different, and these are preferably selected from halogen atoms, methyl groups, methoxy groups and nitro groups. Examples include the o-bromobenzyloxycarbonyl, m-bromobenzyloxycarbonyl, p-bromobenzyloxycarbonyl, o-chlorobenzyloxycarbonyl, m-chlorobenzyloxycarbonyl, p-chlorobenzyloxycarbonyl, 2,4-dichlorobenzyloxycarbonyl, 2,5-dichlorobenzyloxycarbonyl, 3,4-dichlorobenzyloxycarbonyl, p-methylbenzyloxycarbonyl, o-methoxybenzyloxycarbonyl, m-methoxybenzyloxycarbonyl, p-methoxybenzyloxycarbonyl, 2,3-dimethoxybenzyloxycarbonyl, 2,4-dimethoxybenzyloxycarbonyl, 3,4-dimethoxybenzyloxycarbonyl, o-nitrobenzyloxycarbonyl, m-nitrobenzyloxycarbonyl, or p-nitrobenzyloxycarbonyl groups.

Where R or $R^1$ represents a substituted alkoxycarbonyl group, the alkoxy moiety may be straight or branched chain and preferably has from 2 to 6 carbon atoms. There are preferably from 1 to 3 substituents and these are preferably selected from halogen atoms, lower alkoxy groups or chloroethoxy groups. Examples include 2-bromoethoxycarbonyl, 2-chloroethoxycarbonyl, 2-iodoethoxycarbonyl, 2-fluoroethoxycarbonyl, 2,2-dichloroethoxycarbonyl, 2,2,2-trichloroethoxycarbonyl, 2,2,2-trifluoroethoxycarbonyl, 3-chloropropoxycarbonyl, 3-bromopropoxycarbonyl, 1-bromo-2-propoxycarbonyl, 1-chloro-2-propoxycarbonyl, 2,3-dibromopropoxycarbonyl, 2,3-dichloropropoxycarbonyl, 1,3-dibromo-2-propoxycarbonyl, 4-chlorobutoxycarbonyl, 6-chlorohexyloxycarbonyl, 2-methoxyethoxycarbonyl, 2-ethoxyethoxycarbonyl, 2-(2-chloroethoxy)ethoxycarbonyl or 2-butoxyethoxycarbonyl groups.

Where R or $R^1$ represents a cycloalkoxycarbonyl group, which may be substituted or unsubstituted, the substituents (if any) are peferably lower alkyl groups. Examples include cyclopentyloxycarbonyl, cyclohexyloxycarbonyl, 2-methylcyclohexyloxycarbonyl and cycloheptyloxycarbonyl groups.

Where R or $R^1$ represents a heterocyclic methoxycarbonyl group, the heterocyclic moiety is preferably a furyl, pyridyl or thiophene group and examples include 2-furfuryloxycarbonyl, 2-pyridylmethoxycarbonyl, 3-pyridylmethoxycarbonyl, 4-pyridylmethoxycarbonyl and 2-thiophenemethoxycarbonyl groups.

Where R or $R^1$ represents a 3-pyridyloxycarbonyl group, the pyridyl moiety is optionally substituted by one or more halogen atoms and examples of such groups include 3-pyridyloxycarbonyl, 2-bromo-3-pyridyloxycarbonyl and 2-chloro-3-pyridyloxycarbonyl groups.

Where R or $R^1$ represents an alkenyloxycarbonyl group, the alkenyl moiety preferably has 3 or 4 carbon atoms and examples of such groups are allyloxycarbonyl and 3-butenyl-1-oxycarbonyl groups.

Other preferred groups which may be represented by R or $R^1$ are the cyanoacetyl, phenoxycarbonyl and benzyloxycarbonyl groups.

In the above formulae R and $R^1$ most preferably represent: a $C_6$ to $C_{14}$ alkanoyl group; a $C_2$ to $C_4$ haloalkanoyl group; a phenylalkanoyl group in which the alkanoyl moiety has from 2 to 4 carbon atoms; an $C_2$ to $C_7$ alkoxycarbonyl group; a $C_3$ to $C_5$ substituted alkoxycarbonyl group having 1 or 2 halo substituents; a $C_5$ or $C_6$ cycloalkanoyl group; a substituted benzoyl group in which the substituent (preferably at the meta or para position) is a $C_1$ to $C_4$ alkyl group or a halogen atom; a substituted phenoxycarbonyl group having a $C_1$ to $C_4$ alkyl or halo substituent; a benzyloxycarbonyl group; a substituted benzyloxycarbonyl group having 1 or 2 halo or $C_1$ to $C_4$ alkoxy substituents; a heterocyclic carbonyl group in which the heterocyclic ring has a sulphur heteroatom; a toluenesulphonyl group; or a naphthyloxycarbonyl group.

Examples of iodopropargyl derivatives according to the present invention and falling within the scope of the formula (I) or formula (Ia) are listed below. The compounds are hereafter referred to by the numbers assigned to them in this list.

1. 3-Acetoxy-1-iodo-1-propyne
2. 3-Propionyloxy-1-iodo-1-propyne
3. 3-Butyryloxy-1-iodo-1-propyne
4. 3-Isobutyryloxy-1-iodo-1-propyne
5. 3-Pivaloyloxy-1-iodo-1-propyne
6. 3-Valeryloxy-1-iodo-1-propyne
7. 3-Isovaleryloxy-1-iodo-1-propyne
8. 3-(2-Methylbutyryloxy)-1-iodo-1-propyne
9. 3-Hexanoyloxy-1-iodo-1-propyne
10. 3-(2-Methylvaleryloxy)-1-iodo-1-propyne
11. 3-(2-Ethylbutyryloxy)-1-iodo-1-propyne
12. 3-Heptanoyloxy-1-iodo-1-propyne
13. 3-Octanoyloxy-1-iodo-1-propyne
14. 3-(2-Ethylhexanoyloxy)-1-iodo-1-propyne
15. 3-Nonanoyloxy-1-iodo-1-propyne
16. 3-Decanoyloxy-1-iodo-1-propyne
17. 3-Undecanoyloxy-1-iodo-1-propyne
18. 3-Lauroyloxy-1-iodo-1-propyne
19. 3-Myristoyloxy-1-iodo-1-propyne
20. 3-Palmitoyloxy-1-iodo-1-propyne
21. 3-Stearoyloxy-1-iodo-1-propyne
22. 3-Isostearoyloxy-1-iodo-1-propyne
23. 3-Acryloyloxy-1-iodo-1-propyne
24. 3-Methacryloyloxy-1-iodo-1-propyne
25. 3-Crotonoyloxy-1-iodo-1-propyne
26. 3-(3-Butenoyloxy)-1-iodo-1-propyne
27. 3-Sorboyloxy-1-iodo-1-propyne
28. 3-Oleoyloxy-1-iodo-1-propyne
29. 3-(10-Undecenoyloxy)-1-iodo-1-propyne
30. 3-Linolyloxy-1-iodo-1-propyne
31. 3-Bromoacetoxy-1-iodo-1-propyne
32. 3-Chloroacetoxy-1-iodo-1-propyne
33. 3-Dichloroacetoxy-1-iodo-1-propyne
34. 3-Trichloroacetoxy-1-iodo-1-propyne 35. 3-(2-Bromopropionyloxy)-1-iodo-1-propyne
36. 3-(3-Bromopropionyloxy)-1-iodo-1-propyne
37. 3-(2-Chloropropionyloxy)-1-iodo-1-propyne
38. 3-(3-Chloropropionyloxy)-1-iodo-1-propyne
39. 3-(2-Bromobutyryloxy)-1-iodo-1-propyne
40. 3-(4-Chlorobutyryloxy)-1-iodo-1-propyne
41. 3-(2-Chlorobutyryloxy)-1-iodo-1-propyne
42. 3-(3-Chlorobutyryloxy)-1-iodo-1-propyne
43. 3-(2-Bromoisobutyryloxy)-1-iodo-1-propyne
44. 3-(2-Bromoisovaleryloxy)-1-iodo-1-propyne
45. 3-(2-Bromovaleryloxy)-1-iodo-1-propyne
46. 3-(2-Bromohexanoyloxy)-1-iodo-1-propyne
47. 3-(2-Bromooctanoyloxy)-1-iodo-1-propyne
48. 3-(11-Bromoundecanoyloxy)-1-iodo-1-propyne
49. 3-Cyanoacetoxy-1-iodo-1-propyne
50. 3-Cyclohexanecarbonyloxy-1-iodo-1-propyne
51. 3-Cyclopentanecarbonyloxy-1-iodo-1-propyne
52. 3-Cyclobutanecarbonyloxy-1-iodo-1-propyne
53. 3-Phenoxyacetoxy-1-iodo-1-propyne
54. 3-p-Chlorophenoxyacetoxy-1-iodo-1-propyne
55. 3-(2,4-Dichlorophenoxyacetoxy)-1-iodo-1-propyne
3-o-Chlorophenoxyacetoxy-1-iodo-1-propyne
57. 3-p-Bromophenoxyacetoxy-1-iodo-1-propyne
58. 3-(2-Phenoxypropionyloxy)-1-iodo-1-propyne
59. 3-(2-Phenoxybutyryloxy)-1-iodo-1-propyne
60. 3-Phenylacetoxy-1-iodo-1-propyne
61. 3-Cinnamoyloxy-1-iodo-1-propyne
62. 3-(3-Phenylpropionyloxy)-1-iodo-1-propyne
63. 3-Benzoyloxy-1-iodo-1-propyne
64. 3-o-Chlorobenzoyloxy-1-iodo-1-propyne
65. 3-m-Chlorobenzoyloxy-1-iodo-1-propyne
66. 3-p-Chlorobenzoyloxy-1-iodo-1-propyne
67. 3-o-Bromobenzoyloxy-1-iodo-1-propyne
68. 3-m-Bromobenzoyloxy-1-iodo-1-propyne
69. 3-p-Bromobenzoyloxy-1-iodo-1-propyne
70. 3-m-Fluorobenzoyloxy-1-iodo-1-propyne
71. 3-p-Fluorobenzoyloxy-1-iodo-1-propyne
72. 3-(2,4-Dichlorobenzoyloxy)-1-iodo-1-propyne
73. 3-(3,4-Dichlorobenzoyloxy)-1-iodo-1-propyne
74. 3-(3,5-Dichlorobenzoyloxy)-1-iodo-1-propyne
75. 3-o-Iodobenzoyloxy-1-iodo-1-propyne
76. 3-p-Iodobenzoyloxy-1-iodo-1-propyne
77. 3-m-Cyanobenzoyloxy-1-iodo-1-propyne
78. 3-p-Cyanobenzoyloxy-1-iodo-1-propyne
79. 3-o-Methylbenzoyloxy-1-iodo-1-propyne
80. 3-m-Methylbenzoyloxy-1-iodo-1-propyne
81. 3-p-Methylbenzoyloxy-1-iodo-1-propyne
82. 3-m-Nitrobenzoyloxy-1-iodo-1-propyne
83. 3-p-Nitrobenzoyloxy-1-iodo-1-propyne
84. 3-o-Methoxybenzoyloxy-1-iodo-1-propyne
85. 3-m-Methoxybenzoyloxy-1-iodo-1-propyne
86. 3-p-Methoxybenzoyloxy-1-iodo-1-propyne
87. 3-(2,4-Dimethoxybenzoyloxy)-1-iodo-1-propyne
88. 3-(3,4-Dimethoxybenzoyloxy)-1-iodo-1-propyne
89. 3-(3,4-Dimethylbenzoyloxy)-1-iodo-1-propyne
90. 3-(2-Methyl-3-nitrobenzoyloxy)-1-iodo-1-propyne
91. 3-(2-Methyl-6-nitrobenzoyloxy)-1-iodo-1-propyne
92. 3-(3-Methyl-4-nitrobenzoyloxy)-1-iodo-1-propyne
93. 3-(4-Methyl-3-nitrobenzoyloxy)-1-iodo-1-propyne
94. 3-Methoxycarbonyloxy-1-iodo-1-propyne
95. 3-Ethoxycarbonyloxy-1-iodo-1-propyne
96. 3-Propoxycarbonyloxy-1-iodo-1-propyne
97. 3-Isopropoxycarbonyloxy-1-iodo-1-propyne
98. 3-Butoxycarbonyloxy-1-iodo-1-propyne
99. 3-Isobutoxycarbonyloxy-1-iodo-1-propyne
100. 3-sec-Butoxycarbonyloxy-1-iodo-1-propyne
101. 3-Pentyloxycarbonyloxy-1-iodo-1-propyne
102. 3-Isopentyloxycarbonyloxy-1-iodo-1-propyne
103. 3-Hexyloxycarbonyloxy-1-iodo-1-propyne
104. 3-sec-Hexyloxycarbonyloxy-1-iodo-1-propyne
105. 3-(2-Methylpentyloxycarbonyloxy)-1-iodopropyne
106. 3-(4-Methyl-2-pentyloxycarbonyloxy)-1-iodo-1-propyne
107. 3-Heptyloxycarbonyloxy-1-iodo-1-propyne
108. 3-Octyloxycarbonyloxy-1-iodo-1-propyne
109. 3-(2-Ethylhexyloxycarbonyloxy)-1-iodo-1-propyne
110. 3-Nonyloxycarbonyloxy-1-iodo-1-propyne
111. 3-(3,5,5-Trimethylhexyloxycarbonyloxy)-1-iodo-1-propyne
112. 3-Decyloxycarbonyloxy-1-iodo-1-propyne
113. 3-Dodecyloxycarbonyloxy-1-iodo-1-propyne
114. 3-Benzyloxycarbonyloxy-1-iodo-1-propyne
115. 3-Phenoxycarbonyloxy-1-iodo-1-propyne
116. 3-Nicotinoyloxy-1-iodo-1-propyne
117. 3-Isonicotinoyloxy-1-iodo-1-propyne
118. 3-(2-Pyridinecarbonyloxy)-1-iodo-1-propyne
119. 3-(2-Thenoyloxy)-1-iodo-1-propyne
120. 3-(2-Furoyloxy)-1-iodo-1-propyne
121. 3-Benzenesulphonyloxy-1-iodo-1-propyne
122. 3-p-Chlorobenzenesulphonyloxy-1-iodo-1-propyne
123. 3-p-Bromobenzenesulphonyloxy-1-iodo-1-propyne
124. 3-p-Fluorobenzenesulphonyloxy-1-iodo-1-propyne
125. 3-(2,5-Dichlorobenzenesulphonyloxy)-1-iodo-1-propyne
126. 3-p-Toluenesulphonyloxy-1-iodo-1-propyne
127. 3-p-Methoxybenzenesulphonyloxy-1-iodo-1-propyne
128. 3-Propanesulphonyloxy-1-iodo-1-propyne
129. 3-Butanesulphonyloxy-1-iodo-1-propyne
130. 3-Octanesulphonyloxy-1-iodo-1-propyne
131. 3-m-Bromocinnamoyloxy-1-iodo-1-propyne
132. 3-p-Chlorocinnamoyloxy-1-iodo-1-propyne
133. 3-p-Methoxycinnamoyloxy-1-iodo-1-propyne
134. 3-p-Methylcinnamoyloxy-1-iodo-1-propyne
135. 3-o-Nitrocinnamoyloxy-1-iodo-1-propyne
136. 3-o-Bromophenoxycarbonyloxy-1-iodo-1-propyne
137. 3-m-Bromophenoxycarbonyloxy-1-iodo-1-propyne
138. 3-p-Bromophenoxycarbonyloxy-1-iodo-1-propyne
139. 3-o-Chlorophenoxycarbonyloxy-1-iodo-1-propyne
140. 3-m-Chlorophenoxycarbonyloxy-1-iodo-1-propyne
141. 3-p-Chlorophenoxycarbonyloxy-1-iodo-1-propyne
142. 3-o-Fluorophenoxycarbonyloxy-1-iodo-1-propyne
143. 3-m-Fluorophenoxycarbonyloxy-1-iodo-1-propyne
144. 3-p-Fluorophenoxycarbonyloxy-1-iodo-1-propyne
145. 3-(2,3-Dichlorophenoxycarbonyloxy)-1-iodo-1-propyne
146. 3-(2,4-Dichlorophenoxycarbonyloxy)-1-iodo-1-propyne
147. 3-(2,5-Dichlorophenoxycarbonyloxy)-1-iodo-1-propyne
148. 3-(2,6-Dichlorophenoxycarbonyloxy)-1-iodo-1-propyne
149. 3-(3,4-Dichlorophenoxycarbonyloxy)-1-iodo-1-propyne
150. 3-(3,5-Dichlorophenoxycarbonyloxy)-1-iodo-1-propyne
151. 3-(2,3,5-Trichlorophenoxycarbonyloxy)-1-iodo-1-propyne
152. 3-(2,4,5-Trichlorophenoxycarbonyloxy)-1-iodo-1-propyne
153. 3-(2,4,6-Trichlorophenoxycarbonyloxy)-1-iodo-1-propyne
154. 3-(4-sec-Butylphenoxycarbonyloxy)-1-iodo-1-propyne 155. 3-(4-t-Butylphenoxycarbonyloxy)-1-iodo-1-propyne
156. 3-(4-Chloro-2-methylphenoxycarbonyloxy)-1-iodo-1-propyne
157. 3-(4-Chloro-3-methylphenoxycarbonyloxy)-1-iodo-1-propyne
158. 3-o-Methylphenoxycarbonyloxy-1-iodo-1-propyne
159. 3-m-Methylphenoxycarbonyloxy-1-iodo-1-propyne
160. 3-p-Methylphenoxycarbonyloxy-1-iodo-1-propyne
161. 3-(2,3-Dimethylphenoxycarbonyloxy)-1-iodo-1-propyne
162. 3-(2,4-Dimethylphenoxycarbonyloxy)-1-iodo-1-propyne
163. 3-(2,5-Dimethylphenoxycarbonyloxy)-1-iodo-1-propyne
164. 3-(2,6-Dimethylphenoxycarbonyloxy)-1-iodo-1-propyne
165. 3-(3,4-Dimethylphenoxycarbonyloxy)-1-iodo-1-propyne
166. 3-(2,3,5-Trimethylphenoxycarbonyloxy)-1-iodo-1-propyne
167. 3-o-Ethylphenoxycarbonyloxy-1-iodo-1-propyne
168. 3-m-Ethylphenoxycarbonyloxy-1-iodo-1-propyne
169. 3-p-Ethylphenoxycarbonyloxy-1-iodo-1-propyne
170. 3-o-Propylphenoxycarbonyloxy-1-iodo-1-propyne
171. 3-p-Propylphenoxycarbonyloxy-1-iodo-1-propyne
172. 3-o-Methoxyphenoxycarbonyloxy-1-iodo-1-propyne
173. 3-m-Methoxyphenoxycarbonyloxy-1-iodo-1-propyne
174. 3-p-Methoxyphenoxycarbonyloxy-1-iodo-1-propyne
175. 3-o-Nitrophenoxycarbonyloxy-1-iodo-1-propyne
176. 3-m-Nitrophenoxycarbonyloxy-1-iodo-1-propyne
177. 3-p-Nitrophenoxycarbonyloxy-1-iodo-1-propyne
178. 3-(2,4-Dinitrophenoxycarbonyloxy)-1-iodo-1-propyne
179. 3-o-Acetylphenoxycarbonyloxy-1-iodo-1-propyne
180. 3-m-Acetylphenoxycarbonyloxy-1-iodo-1-propyne
181. 3-p-Acetylphenoxycarbonyloxy-1-iodo-1-propyne
182. 3-(3-Methyl-4-nitrophenoxycarbonyloxy)-1-iodo-1-propyne
183. 3-(4-Methyl-2-nitrophenoxycarbonyloxy)-1-iodo-1-propyne
184. 3-(1-Naphthyloxycarbonyloxy)-1-iodo-1-propyne
185. 3-(2-Naphthyloxycarbonyloxy)-1-iodo-1-propyne
186. 3-o-Bromobenzyloxycarbonyloxy-1-iodo-1-propyne
187. 3-m-Bromobenzyloxycarbonyloxy-1-iodo-1-propyne
188. 3-p-Bromobenzyloxycarbonyloxy-1-iodo-1-propyne
189. 3-o-Chlorobenzyloxycarbonyloxy-1-iodo-1-propyne
190. 3-m-Chlorobenzyloxycarbonyloxy-1-iodo-1-propyne
191. 3-p-Chlorobenzyloxycarbonyloxy-1-iodo-1-propyne
192. 3-(2,4-Dichlorobenzyloxycarbonyloxy)-1-iodo-1-propyne
193. 3-(2,5-Dichlorobenzyloxycarbonyloxy)-1-iodo-1-propyne
194. 3-(3,4-Dichlorobenzyloxycarbonyloxy)-1-iodo-1-propyne
195. 3-o-Methoxybenzyloxycarbonyloxy-1-iodo-1-propyne
196. 3-m-Methoxybenzyloxycarbonyloxy-1-iodo-1-propyne
197. 3-p-Methoxybenzyloxycarbonyloxy-1-iodo-1-propyne
198. 3-o-Nitrobenzyloxycarbonyloxy-1-iodo-1-propyne
199. 3-m-Nitrobenzyloxycarbonyloxy-1-iodo-1-propyne
200. 3-p-Nitrobenzyloxycarbonyloxy-1-iodo-1-propyne
201. 3-p-Methylbenzyloxycarbonyloxy-1-iodo-1-propyne
202. 3-(2,3-Dimethoxybenzyloxycarbonyloxy)-1-iodo-1-propyne
203. 3-(2,4-Dimethoxybenzyloxycarbonyloxy)-1-iodo-1-propyne
204. 3-(3,4-Dimethoxybenzyloxycarbonyloxy)-1-iodo-1-propyne
205. 3-(2-Bromoethoxycarbonyloxy)-1-iodo-1-propyne
206. 3-(2-Chloroethoxycarbonyloxy)-1-iodo-1-propyne
207. 3-(2-Iodoethoxycarbonyloxy)-1-iodo-1-propyne
208. 3-(2-Fluoroethoxycarbonyloxy)-1-iodo-1-propyne
209. 3-(2,2-Dichloroethoxycarbonyloxy)-1-iodo-1-propyne
210. 3-(2,2,2-Trichloroethoxycarbonyloxy)-1-iodo-1-propyne
211. 3-(2,2,2-Trifluoroethoxycarbonyloxy)-1-iodo-1-propyne
212. 3-(3-Chloropropoxycarbonyloxy)-1-iodo-1-propyne
213. 3-(3-Bromopropoxycarbonyloxy)-1-iodo-1-propyne
214. 3-(1-Bromo-2-propoxycarbonyloxy)-1-iodo-1-propyne
215. 3-(1-Chloro-2-propoxycarbonyloxy)-1-iodo-1-propyne
216. 3-(2,3-Dibromopropoxycarbonyloxy)-1-iodo-1-propyne
217. 3-(2,3-Dichloropropoxycarbonyloxy)-1-iodo-1-propyne
218. 3-(1,3-Dibromo-2-propoxycarbonyloxy)-1-iodo-1-propyne
219. 3-(4-Chlorobutoxycarbonyloxy)-1-iodo-1-propyne
220. 3-(6-Chlorohexyloxycarbonyloxy)-1-iodo-1-propyne
221. 3-(2-Methoxyethoxycarbonyloxy)-1-iodo-1-propyne
222. 3-(2-Ethoxyethoxycarbonyloxy)-1-iodo-1-propyne
223. 3-[2-(2-Chloroethoxy)ethoxycarbonyloxy]-1-iodo-1-propyne
224. 3-(2-Butoxyethoxycarbonyloxy)-1-iodo-1-propyne
225. 3-(3-Iodopropargyloxycarbonyloxy)-1-iodo-1-propyne
226. 3-Cyclopentyloxycarbonyloxy-1-iodo-1-propyne
227. 3-Cyclohexyloxycarbonyloxy-1-iodo-1-propyne
228. 3-(2-Methylcyclohexyloxycarbonyloxy)-1-iodo-1-propyne
229. 3-Cycloheptyloxycarbonyloxy-1-iodo-1-propyne
230. 3-Furfuryloxycarbonyloxy-1-iodo-1-propyne
231. 3-(2-Pyridylmethyloxycarbonyloxy)-1-iodo-1-propyne
232. 3-(2-Thiophenemethyloxycarbonyloxy)-1-iodo-1-propyne
233. 3-(3-Pyridylmethyloxycarbonyloxy)-1-iodo-1-propyne
234. 3-(4-Pyridylmethyloxycarbonyloxy)-1-iodo-1-propyne
235. 3-(3-Pyridyloxycarbonyloxy)-1-iodo-1-propyne
236. 3-(2-Bromo-3-pyridyloxycarbonyloxy)-1-iodo-1-propyne 237. 3-(2-Chloro-3-pyridyloxycarbonyloxy)-1-iodo-1-propyne
238. 3-Allyloxycarbonyloxy-1-iodo-1-propyne Of the compounds listed above, all are new, except for Compounds 1 and 63, which have been disclosed as already described.

The compounds of the invention may be prepared by reacting 3-hydroxy-1-iodo-1-propyne with an acid halide, chlorocarbonic acid ester or sulphonic acid halide of formula R¹X:

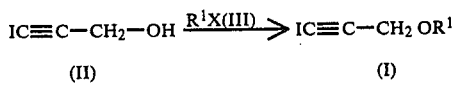

3-Hydroxy-1-iodo-1-propyne is disclosed in U.S. Pat. No. 3,075,938 and may be prepared as described in that U.S. Specification. In the above equation, R¹ is as defined above and X represents a halogen atom. The reaction is preferably carried out in the presence of an inert solvent. There is no particular limitation upon the nature of the solvent employed, provided that it does not adversely affect the reaction. Examples of suitable solvents include: aromatic hydrocarbons, for example benzene, toluene or xylene; aliphatic hydrocarbons, for example hexane or heptane; and cyclic amines, for example pyridine. There is also no particular limitation upon the reaction temperature and, in general, the temperature will be chosen so as to allow the reaction to proceed at a suitable speed; we prefer to employ a reaction temperature between 0° C. and the reflux temperature of the solvent (if any) used. However, for convenience, the reaction is preferably carried out either at room temperature or under ice-cooling.

At the end of the reaction, the desired compound may be separated from the reaction mixture by conventional means. One suitable separation procedure comprises: extracting the desired compound with an organic solvent (for example ethyl acetate); washing the extract with water and then drying it; and finally distilling off the solvent under reduced pressure. If desired, further purification may be carried out by standard techniques, e.g recrystallization or chromatography.

An alternative method of preparing certain of the desired compounds is available where the group R¹ contains a terminal oxycarbonyl moiety, that is to say where R¹ represents a substituted or unsubstituted alkoxycarbonyl group, a substituted or unsubstituted phenoxycarbonyl group, a substituted or unsubstituted benzyloxycarbonyl group, a naphthyloxycarbonyl group, a cycloalkoxycarbonyl group, a heterocyclic methoxycarbonyl group, a substituted or unsubstituted 3-pyridyloxycarbonyl group or an alkenyloxycarbonyl group. In this procedure, 3-hydroxy-1-iodo-1-propyne is reacted with phosgene to produce 3-chlorocarbonyloxy-1-iodo-1-propyne and this is then reacted with a suitable hydroxy group-containing compound to produce the desired compound of formula (I) or (Ia), according to the following reaction scheme:

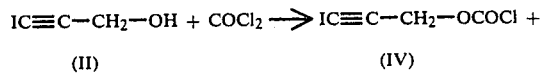

-continued

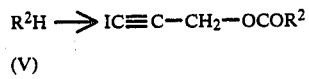

in which R² represents a substituted or unsubstituted alkyl group, a substituted or unsubstituted phenyl group, a substituted or unsubstituted benzyl group, a naphthyl group, an iodopropargyl group, a substituted or unsubstituted cycloalkyl group, a heterocyclicmethyl group, a 3-pyridyl group (optionally halo-substituted) or an alkenyl group.

Each of the two stages of this reaction scheme is preferably carried out in the presence of a suitable inert solvent. There is no particular restriction upon the nature of the solvent, provided that it does not adversely affect the reaction. Suitable solvents which may be employed include: aliphatic hydrocarbons, such as hexane, heptane or octane, aromatic hydrocarbons, such as benzene, toluene or xylene; and cyclic amines, such as pyridine. The solvent in the two stages may be the same or different. We prefer to isolate the compound of formula (IV) produced in the first stage before reacting it, in the second stage, with the compound of formula (V), but this is not necessary.

There is no particular restriction upon the temperature employed for the reaction in both stages of this reaction scheme, although, if the reaction temperature is too low, the reaction time may be unnecessarily prolonged and, if the reaction temperature is too high, production of by-products may increase and low boiling reactants may start to boil off. Accordingly, we prefer that each stage of the reaction should be carried out at a temperature between 0° C. and the reflux temperature of the lowest boiling component of the reaction mixture. For convenience, a temperature of about room temperature is most preferably used.

At the end of the reaction, the desired product may be isolated and purified as described above.

As already explained, the compounds of formula (Ia) are valuable preservative, anti-fungal and termiticidal agents. The invention thus also provides a process for protecting an organic material against deterioration, fungal attack and termite attack, which comprises applying to or into said material a compound of formula (Ia), as defined above.

The invention also provides a preservative, anti-fungal and termiticidal composition comprising, as active ingredient, a compound of formula (Ia) (as defined above) and a suitable carrier.

The compounds of the invention have been found to be effective against a wide range of fungi, particularly those of the genera Penicillium, Aspergillus, Rhizopus, Chaetomium, Cladosporium, Fusarium, and Aureobasideum, as well as a wide variety of other fungi, including those belonging to the genus Trichoderma and wood-staining fungi. However, the use of the compounds of the invention is not restricted to these particular genera of fungi. The compounds of the invention are particularly useful to preserve materials from damage by wood destroying and wood soft rotting fungi.

The compounds of the invention also exhibit a powerful activity against termites, which are parasitic on and injurious to wooden buildings (particularly houses) and general industrial organic materials. The compounds are thus useful as termiticidal agents.

Materials which may be preserved and protected from the harmful effects of fungi or termites by means of the compounds of the invention include, particularly, wood, as well as a variety of industrial materials such as wet pulp, paper, mats, fibres, leather, adhesives, paints and synthetic resins; however, in general, any organic materials susceptible to deterioration by fungal or termite attack may be protected by the compounds of the invention.

The amount of compound of the invention to be applied to the material to be protected may vary over a wide range, depending upon the method of application and on the material to which the compound is applied. In its broadest aspect, the invention envisages employing from 0.1 g to 20 kg of compound per cubic meter of material to be treated. Preferably, where the compound is applied by coating or dipping, the amount employed ranges from 0.1 to 40 g per cubic meter and, where the compound is applied by impregnation, the amount ranges from 20 g to 20 kg per cubic meter. Where the compound of the invention is to be applied principally to the surface of the material to be treated, the amount employed is more conveniently measured in terms of grams per sq. meter of surface area. In these terms, a preferred range is from 0.1 to 40 g per sq. meter, the precise amount depending upon the nature of the material to be treated. Thus, for wood, a preferred amount is from 0.1 to 4 g per sq. meter, for leather 0.1 to 10 g per sq. meter, for paper 0.1 to 2 g per sq. meter and for paint 0.5 to 40 g per sq. meter.

Where the compound of the invention is employed in the form of a composition in admixture with a carrier or adjuvant, the proportion of the compound may vary over a wide range, depending upon the nature of the composition and the material to be treated. In general, the compound of the invention preferably forms from 0.005 to 95% by weight of the composition, this being more preferably from 10 to 75% by weight for emulsifiable concentrates, from 0.005 to 5% by weight for oil-based compositions, from 1 to 95% by weight for dusts and from 2 to 50% by weight for wettable powders.

In general, the composition of the invention may be in the form of oil-soluble preparations, emulsifiable concentrates, pastes, powders, wettable powders, aerosols and paints, as well as many other forms well-known to those skilled in the art.

Suitable carriers include: inert solid carriers, such as clay, talc, bentonite, kaolin, silicic anhydride, calcium carbonate and wood meal; liquid carriers, such as kerosine, ligroin, the xylenes, methylnaphthalene, dimethylformamide and dimethylsulphoxide; and vapour carriers, such as nitrogen gas, dimethyl ether, the vaporizable fluorocarbons and chlorofluorcarbons (such as those sold under the Trade Mark "Freon") and monomeric vinyl chloride. In order to improve the properties of the preparation and/or to enhance the anti-fungal and preservative effects of the composition, any suitable auxiliary agent may be employed in addition to these carriers. Examples include anionic, cationic and non-ionic surface active agents and various high molecular weight compounds, e.g. methylcellulose, vinyl acetate resins and sodium alginate. It is, of course, also possible to enhance the anti-fungal or preservative effect by using the compounds of the invention in admixture with other anti-fungal or preservative agents, such as 2-(4-thiazolyl)benzimidazole (Thiabendazole), N,N-dimethyl-N'-dichlorofluoromethylthio-N'-phenylsulphamide (Dichlorofluanid) or other benzanilides or other wood termiticidal agents, such as Chlordane.

The invention is further illustrated by the following Examples, of which Examples 1 to 5 illustrate the preparation of compounds according to the invention, Examples 6 to 11 illustrate the anti-fungal and termiticidal effect of the compounds and the remaining Examples illustrate preservative, anti-fungal and termiticidal compositions containing the compounds of the invention.

EXAMPLE 1

Preparation of 3-myristoyloxy-1-iodo-1-propyne (Compound 19)

1.4 g of myristoyl chloride were added, with cooling, to a solution of 1.0 g of 3-hydroxy-1-iodo-1-propyne (iodopropargyl alcohol) in 2 ml of pyridine, and the reaction mixture was left overnight. The mixture was then poured into ice-water and extracted with ethyl acetate. The extract was washed with water and dried over anhydrous sodium sulphate, and then the solvent was distilled off under reduced pressure. The resulting oily substance was fractionated and purified by silica gel column chromatography eluted with a 3:1 by volume mixture of n-hexane and ethyl acetate. 1.8 g of the desired Compound 19 were obtained, melting point 39°–40° C.

Elemental Analysis:

Calculated for $C_{17}H_{29}O_2I$: C, 52.05%; H, 7.45%; I, 32.35%. Found: C, 52.06%, H, 7.55%; I, 32.50%.

EXAMPLE 2

Preparation of 3-ethoxycarbonyloxy-iodo-1-propyne (Compound 95)

1.1 g of ethyl chloroformate were added dropwise to a solution of 2.0 g of 3-hydroxy-1-iodo-1-propyne in 3.5 ml of pyridine and the mixture was stirred at room temperature for 1 hour. The reaction mixture was then poured into ice-water and subsequently treated as described in Example 1 to give 2.5 g of the desired Compound 95 as an oily product.

Infra-red absorption spectrum (Liquid film) $vcm^{-1}$: 2210, 1755.

Elemental Analysis:

Calculated for $C_6H_7O_3I$: C, 28.36%; H, 2.77%; I, 49.95%. Found: C, 28.51%; H, 2.86%; I, 49.93%.

EXAMPLE 3

Preparation of 3-p-toluenesulphonyloxy-1-iodo-1-propyne (Compound 126)

A solution of 0.2 g of sodium hydroxide in 1 ml of water was added, with stirring, at room temperature to a solution of 1.0 g of 3-hydroxy-1-iodo-1-propyne and 1.0 g of p-toluenesulphonyl chloride in dioxan. After stirring the mixture for 30 minutes, it was poured into ice-water and the mixture was extracted with diethyl ether. The extract was washed with water and dried over anhydrous sodium sulphate, and then the solvent was distilled off under reduced pressure. The oily substance thus obtained was fractionated and purified by silica gel column chromatography eluted with a 3:1 by volume mixture of n-hexane and ethyl acetate. 1.47 g of the desired Compound 126 were obtained in the form of a semi-solid.

Infra-red absorption spectrum (liquid film) νcm⁻¹: 2200.

Elemental Analysis:
Calculated for $C_{10}H_9O_3SI$: C, 35.73%; H, 2.70%; S, 9.54%; I, 37.75%. Found: C, 35.68%; H, 2.74%; S, 9.31%; I, 38.05%.

EXAMPLE 4

Preparation of 3-p-bromophenoxycarbonyloxy-1-iodo-1-propyne (Compound 138)

20 ml of a 10% w/v benzene solution of phosgene were added to a solution of 1.8 g of 3-hydroxy-1-iodo-1-propyne in 20 ml of benzene, and then 6.05 g of pyridine were added dropwise thereto. The resulting mixture was stirred at room temperature for 3 hours and then left overnight. At the end of this time, the solvent was distilled off under reduced pressure, leaving 2.4 g of an oily substance, which was disolved in 5 ml of cooled pyridine. 1.7 g of p-bromophenol were added thereto and the mixture thus obtained was stirred at room temperature for 3 hours. The reaction mixture was then poured into cold water and extracted with ethyl acetate. The extract was washed with water and dried over anhydrous sodium sulphate, and then the solvent was distilled off under reduced pressure, giving an oily substance. This substance was then fractionated and purified by silica gel column chromatography eluted with a 3:1 by volume mixture of n-hexane and ethyl acetate, giving 1.8 g of the desired Compound 138, melting point 110°–111° C.

Elemental Analysis:
Calculated for $C_{10}H_6O_3BrI$: C, 31.53%; H, 1.59%; Br, 20.97%; I, 33.31%. Found: C, 31.46%; H, 1.45%; Br, 20.69%; I, 33.04%.

EXAMPLE 5

Preparation of 3-p-bromophenoxycarbonyloxy-1-iodo-1-propyne (Compound 138)

2.4 g of p-bromophenoxychloroformate [J. Org. Chem. 32, 300–307 (1967)] were added dropwise to a solution of 1.8 g of 3-hydroxy-1-iodo-1-propyne in 4 ml of pyridine and the resulting mixture was stirred at room temperature for 1 hour. The mixture was then poured into ice-water and subsequently treated and purified as described in Example 4, giving 2.3 g of the desired Compound 138, melting point 110°–111° C.

Elemental Analysis:
Calculated for $C_{10}H_6O_3BrI$: C, 31.53%; H, 1.59%; Br, 20.97%; I, 33.31%. Found: C, 31.48%; H, 1.60%; Br, 20.95%; I, 33.30.

Following the procedures described in the above Examples, the following compounds were also prepared; their properties are briefly summarized in the following Table and the compounds are identified by the numbers previously assigned to them.

| Compound No. | Melting point (°C.) or Physical State. | Infra-red spectrum (cm⁻¹). | Analysis (%) Upper column: calculated Lower column: Found |
|---|---|---|---|
| 1 | 53–4 | 2200 | C,26.81; H,2.25; I,56.65 |
|   |      | 1725 | C,27.11; H,2.29; I,56.81 |
| 2 | Oily | 2200 | C,30.27; H,2.97; I,53.31 |
|   |      | 1740 | C,30.15; H,3.00; I,53.47 |
| 3 | Oily | 2200 | C,33.36; H,3.60; I,50.35 |
|   |      | 1740 | C,33.08; H,3.61; I,50.50 |
| 4 | Oily | 2200 | C,33.36; H,3.60; I,50.35 |
|   |      | 1740 | C,33.53; H,3.71; I,50.22 |
| 5 | Oily | 2200 | C,36.11; H,4.17; I,47.69 |
|   |      | 1730 | C,36.25; H,4.30; I,47.87 |
| 7 | Oily | 2200 | C,36.11; H,4.17; I,47.69 |
|   |      | 1740 | C,36.34; H,4.21; I,47.63 |
| 9 | Oily | 2200 | C,38.59; H,4.68; I,45.31 |
|   |      | 1750 | C,38.38; H,4.71; I,45.22 |
| 16 | Oily | 2200 | C,46.44; H,6.30; I,37.74 |
|    |      | 1750 | C,46.42; H,6.09; I,37.56 |
| 18 | 32–3 | 2210 | C,49.46; H,6.92; I,34.84 |
|    |      | 1750 | C,49.39; H,7.03; I,34.92 |
| 20 | 42–3 | 2180 | C,54.29; H,7.91; I,30.19 |
|    |      | 1720 | C,54.58; H,8.07; I,29.92 |
|    |      | 1710 |                          |
| 21 | 57–9 | 2200 | C,56.25; H,8.32; I,28.30 |
|    |      | 1730 | C,56.44; H,8.26; I,28.46 |
| 23 | Oily | 2200 | C,30.53; H,2.14; I,53.37 |
|    |      | 1730 | C,30.45; H,2.24; I,53.57 |
| 25 | 52–3 | 2200 | C,33.62; H,2.82; I,50.75 |
|    |      | 1710 | C,33.42; H,2.78; I,50.98 |
| 27 | 65–6 | 2200 | C,39.15; H,3.29; I,45.97 |
|    |      | 1700 | C,38.95; H,3.09; I,45.86 |
| 28 | Oily | 2200 | C,56.50; H,7.90; I,28.43 |
|    |      | 1750 | C,56.71; H,7.76; I,28.42 |
| 31 | Oily | 2200 | C,19.83; H,1.33; I,41.90 |
|    |      | 1740 | C,19.76; H,1.31; I,41.82 |
| 32 | Oily | 2200 | C,23.24; H,1.56; I,49.10 |
|    |      | 1740 | C,23.06; H,1.62; I,49.00 |
| 35 | Oily | 2200 | C,22.74; H,1.91; I,40.04 |
|    |      | 1740 | C,22.89; H,1.97; I,40.25 |
| 39 | Oily | 2200 | C,25.40; H,2.44; I,38.35 |
|    |      | 1740 | C,25.54; H,2.49; I,38.50 |
| 40 | Oily | 2180 | C,29.35; H,2.81; I,44.30 |
|    |      | 1740 | C,29.44; H,2.83; I,44.19 |
| 43 | Oily | 2200 | C,25.40; H,2.44; I,38.35 |
|    |      | 1740 | C,25.53; H,2.55; I,38.47 |
| 49 | 80–1 | 2200 | C,28.94; H,1.62; I,50.96 |
|    |      | 1740 | C,29.01; H,1.63; I,51.01 |
| 50 | Oily | 2170 | C,41.12; H,4.48; I,43.44 |
|    |      | 1730 | C,41.13; H,4.42; I,43.31 |
| 53 | Oily | 2225 | C,41.80; H,2.87; I,40.15 |
|    |      | 1770 | C,41.75; H,2.85; I,40.16 |
| 54 | 49–51 | 2200 | C,37.69; H,2.30; I,36.20 |
|    |       | 1765 | C,37.86; H,2.36; I,36.13 |
| 56 | Oily | 2200 | C,37.69; H,2.30; I,36.20 |
|    |      | 1760 | C,37.59; H,2.23; I,36.15 |
| 58 | Oily | 2200 | C,43.66; H,3.36; I,38.44 |
|    |      | 1760 | C,43.52; H,3.16; I,38.28 |
| 60 | Oily | 2180 | C,44.03; H,3.02; I,42.29 |
|    |      | 1740 | C,44.12; H,3.12; I,42.10 |
| 61 | 56–7 | 2200 | C,46.18; H,2.91; I,40.66 |
|    |      | 1700 | C,46.10; H,2.78; I,40.63 |
| 62 | Oily | 2150 | C,45.88; H,3.53; I,40.40 |
|    |      | 1740 | C,45.90; H,3.69; I,40.51 |
| 63 | 54–6 | 2200 | C,41.99; H,2.47; I,44.36 |
|    |      | 1725 | C,42.18; H,2.50; I,44.32 |
| 64 | 46–8 | 2210 | C,37.47; H,1.89; I,39.59 |
|    |      | 1730 | C,37.69; H,1.97; I,39.39 |
| 65 | 51–2 | 2200 | C,37.47; H,1.89; I,39.59 |
|    |      | 1720 | C,37.46; H,1.86; I,39.49 |
| 66 | 63–4 | 2200 | C,37.47; H,1.89; I,39.59 |
|    |      | 1715 | C,37.26; H,2.02; I,39.47 |
| 68 | 41–2 | 2220 | C,32.91; H,1.66; I,34.77 |
|    |      | 1720 | C,33.13; H,1.67; I,35.02 |
| 69 | 82–4 | 2200 | C,32.91; H,1.66; I,34.77 |
|    |      | 1730 | C,32.98; H,1.73; I,34.67 |
| 72 | Oily | 2220 | C,33.84; H,1.42; I,35.75 |
|    |      | 1740 | C,34.07; H,1.51; I,35.69 |
| 73 | 69–71 | 2220 | C,33.84; H,1.42; I,35.75 |
|    |       | 1735 | C,33.69; H,1.36; I,35.50 |
| 74 | 86–8 | 2180 | C,33.84; H,1.42; I,35.75 |
|    |      | 1730 | C,34.14; H,1.45; I,35.50 |
| 78 | 119–221 | 2200 | C,42.47; H,1.94; I,40.79 |

| Compound No. | Melting point. (°C.) or Physical State. | Infra-red spectrum (cm⁻¹). | Analysis (%) Upper column: calculated Lower column: Found |
|---|---|---|---|
| 79 | 49–50 | 1730<br>2200<br>1710 | C,42.50; H,1.95; I,40.73<br>C,44.03; H,3.02; I,42.29<br>C,44.15; H,3.11; I,42.20 |
| 80 | 39–40 | 2180<br>1715 | C,44.03; H,3.02; I,42.29<br>C,43.80; H,3.10; I,42.34 |
| 81 | 97–8 | 2200<br>1710 | C,44.03; H,3.02; I,42.29<br>C,43.97; H,2.85; I,42.03 |
| 82 | 86–8 | 2200<br>1740 | C,36.28; H,1.83; I,38.33<br>C,36.30; H,1.96; I,38.31 |
| 83 | 145–7 | 2200<br>1730 | C,36.28; H,1.83; I,38.33<br>C,36.32; H,1.72; I,38.28 |
| 84 | 91–2 | 2200<br>1720 | C,41.80; H,2.87; I,40.15<br>C,41.66; H,2.80; I,39.91 |
| 86 | 103–5 | 2200<br>1710 | C,41.80; H,2.87; I,40.15<br>C,41.99; H,2.75; I,40.13 |
| 94 | 40–1 | 2200<br>1750 | C,25.02; H,2.10; I,52.88<br>C,25.01; H,2.14; I,52.96 |
| 98 | Oily | 2180<br>1750 | C,34.06; H,3.93; I,44.99<br>C,34.29; H,4.13; I,44.72 |
| 99 | Oily | 2180<br>1750 | C,34.06; H,3.93; I,44.99<br>C,34.34; H,4.06; I,44.88 |
| 103 | Oily | 2200<br>1750 | C,38.73; H,4.88; I,40.92<br>C,39.01; H,4.99; I,40.78 |
| 110 | Oily | 2200<br>1750 | C,44.33; H,6.01; I,36.03<br>C,44.47; H,6.10; I,35.93 |
| 114 | Oily | 2180<br>1750 | C,41.80; H,2.87; I,40.15<br>C,42.00; H,2.98; I,39.96 |
| 115 | 50–2 | 2210<br>1710 | C,39.76; H,2.34; I,42.01<br>C,40.00; H,2.40; I,42.05 |
| 116 | 156–8 | 2200<br>1720 | C,37.66; H,2.11; I,44.21<br>C,37.56; H,2.07; I,44.12 |
| 117 | 143–5 | 2180<br>1730 | C,37.66; H,2.11; I,44.21<br>C,37.62; H,2.02; I,44.50 |
| 118 | 139–140 | 2200<br>1740 | C,37.66; H,2.11; I,44.21<br>C,37.85; H,2.03; I,44.03 |
| 119 | 55–6 | 2200<br>1710 | C,32.90; H,1.73; I,43.45<br>C,32.80; H,1.72; I,43.32 |
| 120 | 55–6 | 2200<br>1690 | C,34.81; H,1.83; I,45.97<br>C,34.44; H,1.70; I,46.06 |
| 121 | Oily | 2200 | C,33.56; H,2.19; I,39.40<br>C,33.67; H,2.37; I,39.48 |
| 122 | 58–9 | 2190 | C,30.32; H,1.70; I,35.59<br>C,30.45; H,1.92; I,35.40 |
| 129 | Oily | 2200 | C,27.83; H,3.67; I,42.00<br>C,27.63; H,3.78; I,42.11 |
| 136 | Oily | 2200<br>1765 | C,31.53; H,1.59; Br,20.98; I,33.31<br>C,31.26; H,1.62; Br,20.97; I,33.48 |
| 139 | 71–72 | 2175<br>1750 | C,35.69; H,1.80; Cl,10.53; I,37.71<br>C,35.52; H,1.66; Cl,10.53; I,37.93 |
| 146 | 121–122 | 2200<br>1740 | C,32.38; H,1.36; Cl,19.11; I,34.21<br>C,32.26; H,1.22; Cl,19.18; I,34.49 |
| 152 | 100–101 | 2180<br>1735 | C,29.70; H,0.99; Cl,26.29; I,31.38<br>C,29.56; H,0.98; Cl,26.26; I,31.12 |
| 155 | Oily | 2200<br>1770 | C,46.95; H,4.22; I,35.43<br>C,46.72; H,4.13; I,35.51 |
| 160 | 106–107 | 2160<br>1745 | C,41.80; H,2.87; I,40.15<br>C,41.90; H,2.70; I,39.94 |
| 172 | Oily | 2200<br>1765 | C,39.78; H,2.73; I,38.21<br>C,39.87; H,2.85; I,38.11 |
| 173 | 74–75 | 2200<br>1760 | C,39.78; H,2.73; I,38.21<br>C,39.89; H,2.70; I,38.46 |
| 174 | 98–99 | 2200<br>1780 | C,39.78; H,2.73; I,38.21<br>C,39.80; H,2.62; I,38.09 |
| 177 | 125–126 | 2200<br>1760 | C,34.61; H,1.74; N,4.04; I,36.56<br>C,34.56; H,1.85; N,4.12; I,36.26 |
| 178 | 131–132 | 2180<br>1780 | C,30.64; H,1.29; N,7.04; I,32.37<br>C,30.77; H,1.24; N,6.93; I,32.37 |
| 181 | 134–136 | 2180<br>1765<br>1670 | C,41.89; H,2.64; I,36.88<br>C,41.91; H,2.67; I,36.61 |
| 184 | 106–107 | 2180<br>1745 | C,47.75; H,2.58; I,36.04<br>C,47.46; H,2.56; I,36.29 |
| 185 | 84–85 | 2200<br>1750 | C,47.75; H,2.58; I,36.04<br>C,47.48; H,2.75; I,36.25 |
| 186 | Oily | 2200<br>1750 | C,33.45; H,2.04; Br,20.23; I,32.13<br>C,33.59; H,2.13; Br,20.21; I,32.25 |
| 189 | Oily | 2200 | C,37.69; H,2.30; Cl,10.11; I,36.20 |
| 190 | Oily | 1750<br>2200<br>1750 | C,37.78; H,2.33; Cl,10.33; I,36.18<br>C,37.69; H,2.30; Cl,10.11; I,36.20<br>C,37.46; H,2.31; Cl,10.17; I,36.42 |
| 191 | 128–129 | 2200<br>1760 | C,37.69; H,2.30; Cl,10.11; I,36.20<br>C,37.45; H,2.34; Cl,10.32; I,36.50 |
| 192 | Oily | 2200<br>1750 | C,34.32; H,1.83; Cl,18.42; I,32.96<br>C,34.60; H,2.05; Cl,18.55; I,33.23 |
| 195 | Oily | 2180<br>1750 | C,41.64; H,3.20; I,36.67<br>C,41.94; H,3.22; I,36.97 |
| 196 | Oily | 2180<br>1750 | C,41.64; H,3.20; I,36.67<br>C,41.47; H,3.03; I,36.46 |
| 197 | 124–125 | 2200<br>1740 | C,41.64; H,3.20; I,36.67<br>C,41.54; H,3.15; I,36.57 |
| 200 | 74–75 | 2180<br>1745 | C,36.58; H,2.23; N,3.87; I,35.43<br>C,36.76; H,2.19; N,3.67; I,35.20 |
| 201 | Oily | 2170<br>1750 | C,43.66; H,3.36; I,38.44<br>C,43.73; H,3.23; I,38.64 |
| 204 | 98–99 | 2180<br>1735 | C,41.51; H,3.48; I,33.73<br>C,41.48; H,3.37; I,33.71 |
| 205 | Oily | 2200<br>1750 | C,21.64; H,1.82; Br,24.00; I,38.12<br>C,21.75; H,1.91; Br,24.23; I,38.25 |
| 206 | Oily | 2200<br>1760 | C,24.98; H,2.10; Cl,12.29; I,43.99<br>C,24.76; H,2.15; Cl,12.10; I,43.81 |
| 210 | Oily | 2180<br>1760 | C,20.16; H,1.12; Cl,29.76; I,35.51<br>C,19.99; H,1.17; Cl,29.59; I,35.47 |
| 212 | Oily | 2175<br>1740 | C,27.80; H,2.66; Cl,11.72; I,41.95<br>C,27.60; H,2.65; Cl,11.52; I,41.85 |
| 214 | Oily | 2200<br>1760 | C,24.23; H,2.32; Br,23.03; I,36.58<br>C,24.50; H,2.15; Br,23.31; I,36.50 |
| 218 | Oily | 2200<br>1750 | C,19.72; H,1.64; Br,37.52; I,29.80<br>C,19.80; H,1.64; Br,37.29; I,29.54 |
| 219 | Oily | 2200<br>1750 | C,30.36; H,3.18; Cl,11.20; I,40.09<br>C,30.28; H,3.08; Cl,11.26; I,40.28 |
| 220 | Oily | 2200<br>1750 | C,34.83; H,4.06; Cl,10.30; I,36.87<br>C,34.65; H,3.76; Cl,10.30; I,36.91 |
| 221 | Oily | 2180<br>1750 | C,29.59; H,3.19; I,44.68<br>C,29.33; H,3.18; I,44.49 |
| 222 | Oily | 2200<br>1760 | C,32.23; H,3.72; I,42.57<br>C,32.44; H,3.85; I,42.77 |
| 223 | Oily | 2200<br>1750 | C,28.90; H,3.03; Cl,10.66; I,38.16<br>C,28.75; H,3.10; Cl,10.50; I,38.01 |
| 224 | Oily | 2200<br>1750 | C,36.83; H,4.64; I,38.91<br>C,36.76; H,4.75; I,38.85 |
| 225 | 128–129 | 2200<br>1750 | C,21.56; H,1.03; I,65.09<br>C,21.81; H,1.11; I,65.34 |
| 226 | Oily | 2180<br>1750 | C,36.75; H,3.77; I,43.15<br>C,36.46; H,3.77; I,43.37 |
| 227 | Oily | 2170<br>1740 | C,38.98; H,4.25; I,41.18<br>C,38.72; H,4.02; I,41.02 |
| 228 | Oily | 2180<br>1750 | C,41.02; H,4.69; I,39.39<br>C,40.79; H,4.50; I,39.60 |
| 230 | Oily | 2180<br>1750 | C,35.23; H,2.30; I,41.46<br>C,35.54; H,2.17; I,41.44 |
| 231 | 125 | 2175<br>1750 | C,37.88; H,2.54; N,4.42; I,40.02<br>C,37.93; H,2.50; N,4.33; I,40.27 |
| 233 | 129–130 | 2200<br>1760 | C,37.88; H,2.54; N,4.42; I,40.02<br>C,37.69; H,2.45; N,4.26; I,40.32 |
| 234 | 127–128 | 2175<br>1750 | C,37.88; H,2.54; N,4.42; I,40.02<br>C,37.69; H,2.49; N,4.67; I,40.05 |
| 236 | 148–150 | 2180<br>1765 | C,28.30; H,1.31; N,3.67; I,33.22<br>C,28.28; H,1.43; N,3.58; I,32.48 |
| 238 | Oily | 2200<br>1750 | C,31.60; H,2.65; I,47.70<br>C,31.53; H,2.67; I,47.50 |

EXAMPLE 6

Test for anti-fungal activity

In this test, the anti-fungal activities of compounds according to the present invention are evaluated and compared with the anti-fungal activity of a known anti-fungal agent, pentachlorophenol laurate (PCP laurate). The test samples were pieces of sapwood (each 2×2×0.5 cm) from bamboo (*Phyllostachys mitis*) and beech (*Fagus Sieboldi*). Each wooden test sample was dipped into a 0.5% w/v dimethylformamide solution containing one of the test compounds shown in the following Table 1 for 5 seconds, air-dried, washed with water (at a rate of supply about 2 liters/minute) for 1 hour, air-dried for 24 hours and then subjected to a weather-proofing test by heating at 60° C. for 24 hours and treating by dry air sterilization.

Each test sample was then tested for its resistance to fungal attack by the procedure prescribed by Japanese Industrial Standard Z2911 ("Anti-fungal Tests"). Specifically, each wooden test sample was subjected to one of the following test fungi:

*Aspergillus flavus* (Test fungus No. 1)
*Penicillium luteum* (Test fungus No. 2)
*Rhizopus nigricans* (Test fungus No. 3)
*Fusarium moniriforme* (Test fungus No. 4)
*Pullularia pullulans* (Test fungus No. 5)
*Chaetomium globosum* (Test fungus No. 6)
*Cladosporium herbarum* (Test fungus No. 7).

A suspension of the wooden test fungus was inoculated into the wooden test sample and then cultivated at 25° C. for 3 weeks in a sterile Petri dish containing a wet filter paper. The growth of the mycelium was evaluated and the results are shown in Table 1 using the following ratings:

| | |
|---|---|
| +: | No growth of fungus on test sample observed; |
| ±: | Only slight growth of fungus observed on test sample; |
| −: | growth of fungus on test sample observed |

Samples of untreated wood were also inoculated with fungus and the growth of fungus under the same conditions was observed and is also reported in Table 1.

TABLE 1

| | Antifungal effect | | | | | | | | | | | | | |
|---|---|---|---|---|---|---|---|---|---|---|---|---|---|---|
| | Bamboo Test fungus No. | | | | | | | Beech Test fungus No. | | | | | | |
| Compound No. | 1 | 2 | 3 | 4 | 5 | 6 | 7 | 1 | 2 | 3 | 4 | 5 | 6 | 7 |
| 1 | + | + | + | + | + | + | + | + | + | + | + | + | + | + |
| 2 | + | + | + | + | + | + | + | + | + | + | + | + | + | + |
| 3 | + | + | + | + | + | + | + | + | + | + | + | + | + | + |
| 4 | + | + | + | + | + | + | + | + | + | + | + | + | + | + |
| 5 | + | + | + | + | + | + | + | + | + | + | + | + | + | + |
| 7 | + | + | + | + | + | + | + | + | + | + | + | + | + | + |
| 9 | + | + | + | + | + | + | + | + | + | + | + | + | + | + |
| 16 | + | + | + | + | + | + | + | + | + | + | + | + | + | + |
| 18 | + | + | + | + | + | + | + | + | + | + | + | + | + | + |
| 19 | + | + | + | + | + | + | + | + | + | + | + | + | + | + |
| 20 | + | + | + | + | + | + | + | + | + | + | + | + | + | + |
| 21 | + | + | + | + | + | + | + | + | + | + | + | + | + | + |
| 23 | + | + | + | + | + | + | + | + | + | + | + | + | + | + |
| 25 | + | + | + | + | + | + | + | + | + | + | + | + | + | + |
| 27 | + | + | + | + | + | + | + | + | + | + | + | + | + | + |
| 28 | + | + | + | + | + | + | + | + | + | + | + | + | + | + |
| 31 | + | + | + | + | + | + | + | + | + | + | + | + | + | + |
| 32 | + | + | + | + | + | + | + | + | + | + | + | + | + | + |
| 35 | + | + | + | + | + | + | + | + | + | + | + | + | + | + |
| 39 | + | + | + | + | + | + | + | + | + | + | + | + | + | + |
| 40 | + | + | + | + | + | + | + | + | + | + | + | + | + | + |
| 43 | + | + | + | + | + | + | + | + | + | + | + | + | + | + |
| 49 | + | + | + | + | + | + | + | + | + | + | + | + | + | + |
| 50 | + | + | + | + | + | + | + | + | + | + | + | + | + | + |
| 53 | + | + | + | + | + | + | + | + | + | + | + | + | + | + |
| 54 | + | + | + | + | + | + | + | + | + | + | + | + | + | + |
| 56 | + | + | + | + | + | + | + | + | + | + | + | + | + | + |
| 58 | + | + | + | + | + | + | + | + | + | + | + | + | + | + |
| 60 | + | + | + | + | + | + | + | + | + | + | + | + | + | + |
| 61 | + | + | + | + | + | + | + | + | + | + | + | + | + | + |
| 62 | + | + | + | + | + | + | + | + | + | + | + | + | + | + |
| 63 | + | + | + | ± | ± | + | ± | + | + | + | + | ± | + | ± |
| 64 | + | ± | ± | + | + | ± | ± | + | ± | + | + | + | + | + |
| 65 | + | + | + | + | + | + | + | + | + | + | + | + | + | + |
| 66 | + | + | + | + | + | + | + | + | + | + | + | + | + | + |
| 68 | + | + | + | + | + | + | + | + | + | + | + | + | + | + |
| 69 | + | + | + | + | + | + | + | + | + | + | + | + | + | + |
| 72 | − | + | ± | ± | + | ± | ± | − | + | ± | + | + | + | ± |
| 73 | + | + | ± | + | + | + | + | + | + | + | + | + | + | + |
| 74 | ± | + | ± | ± | ± | ± | ± | + | + | + | + | + | + | ± |
| 78 | + | + | + | + | + | + | + | + | + | + | + | + | + | + |
| 79 | ± | + | ± | − | + | ± | ± | ± | + | ± | − | + | + | + |
| 80 | + | + | + | + | + | + | + | + | + | + | + | + | + | + |
| 81 | + | + | ± | + | + | + | + | + | + | ± | + | + | + | + |
| 82 | + | + | + | ± | + | + | ± | + | + | ± | + | + | + | + |
| 83 | + | + | + | + | + | + | + | + | + | + | + | + | + | + |
| 84 | ± | + | ± | ± | + | ± | ± | ± | + | ± | + | + | + | ± |
| 86 | + | + | + | + | + | + | + | + | + | + | + | + | + | + |
| 94 | + | + | + | + | + | + | + | + | + | + | + | + | + | + |
| 95 | + | + | + | + | + | + | + | + | + | + | + | + | + | + |
| 98 | + | + | + | + | + | + | + | + | + | + | + | + | + | + |
| 99 | + | + | ± | + | + | + | + | + | + | ± | + | + | + | + |
| 103 | + | + | + | + | + | + | + | + | + | + | + | + | + | + |
| 110 | + | + | − | + | + | + | ± | + | + | − | + | + | + | + |
| 114 | + | + | + | + | + | + | + | + | + | + | + | + | + | + |

TABLE 1-continued

| | Antifungal effect | | | | | | | | | | | | | |
|---|---|---|---|---|---|---|---|---|---|---|---|---|---|
| | Bamboo Test fungus No. | | | | | | | Beech Test fungus No. | | | | | | |
| Compound No. | 1 | 2 | 3 | 4 | 5 | 6 | 7 | 1 | 2 | 3 | 4 | 5 | 6 | 7 |
| 115 | + | + | + | + | + | + | + | + | + | + | + | + | + | + |
| 116 | + | + | + | + | + | + | + | + | + | + | + | + | + | + |
| 117 | + | + | + | + | + | + | + | + | + | + | + | + | + | + |
| 118 | + | + | + | + | + | + | + | + | + | + | + | + | + | + |
| 119 | + | + | + | + | + | + | + | + | + | + | + | + | + | + |
| 120 | + | − | + | ± | + | + | ± | + | − | + | + | + | + | + |
| 121 | + | + | ± | + | + | + | + | + | + | + | + | + | + | + |
| 122 | + | + | + | + | + | + | + | + | + | + | + | + | + | + |
| 126 | + | + | + | + | + | + | + | + | + | + | + | + | + | + |
| 129 | + | + | + | + | + | + | + | + | + | + | + | + | + | + |
| 136 | + | + | + | + | + | + | + | + | + | + | + | + | + | + |
| 138 | + | + | + | + | + | + | + | + | + | + | + | + | + | + |
| 139 | + | + | + | + | + | + | + | + | + | + | + | + | + | + |
| 146 | + | + | + | + | + | + | + | + | + | + | + | + | + | + |
| 152 | + | + | + | + | + | + | + | + | + | + | + | + | + | + |
| 155 | + | + | ± | + | + | ± | + | + | + | + | + | + | + | + |
| 160 | + | + | + | + | + | + | + | + | + | + | + | + | + | + |
| 172 | + | + | − | ± | + | ± | ± | + | + | − | + | + | ± | + |
| 173 | + | + | + | + | + | + | + | + | + | + | + | + | + | + |
| 174 | + | + | + | + | + | + | + | + | + | + | + | + | + | + |
| 177 | + | + | + | + | + | + | + | + | + | + | + | + | + | + |
| 178 | + | + | − | + | ± | ± | + | + | + | ± | + | + | + | + |
| 181 | + | + | + | + | + | + | + | + | + | + | + | + | + | + |
| 184 | + | + | + | + | + | + | + | + | + | + | + | + | + | + |
| 185 | + | + | + | + | + | + | + | + | + | + | + | + | + | + |
| 190 | + | + | ± | + | + | ± | + | + | + | + | + | + | + | + |
| 192 | + | + | + | + | + | + | + | + | + | + | + | + | + | + |
| 195 | + | + | + | + | + | + | + | + | + | + | + | + | + | + |
| 196 | ± | + | − | + | + | ± | + | + | + | ± | + | + | ± | + |
| 197 | + | + | + | + | + | + | + | + | + | + | + | + | + | + |
| 200 | + | + | − | + | ± | + | + | + | + | ± | + | + | + | + |
| 201 | + | + | ± | + | + | + | + | + | + | + | + | + | + | + |
| 204 | + | + | + | + | + | + | + | + | + | + | + | + | + | + |
| 205 | + | + | + | + | + | + | + | + | + | + | + | + | + | + |
| 206 | + | + | + | + | + | + | + | + | + | + | + | + | + | + |
| 210 | + | + | + | + | + | + | + | + | + | + | + | + | + | + |
| 212 | + | + | + | + | + | + | + | + | + | + | + | + | + | + |
| 214 | + | + | + | + | + | + | + | + | + | + | + | + | + | + |
| 218 | + | + | + | + | + | + | + | + | + | + | + | + | + | + |
| 219 | + | + | + | + | + | + | + | + | + | + | + | + | + | + |
| 221 | + | + | + | + | + | + | + | + | + | + | + | + | + | + |
| 222 | + | + | − | ± | + | + | + | + | + | − | + | + | + | + |
| 223 | + | + | + | + | + | + | + | + | + | + | + | + | + | + |
| 224 | + | + | − | ± | − | ± | ± | + | + | ± | + | + | + | + |
| 225 | + | + | − | + | + | ± | + | + | + | ± | + | + | + | + |
| 226 | + | + | − | + | + | ± | + | + | + | − | + | + | + | + |
| 230 | + | + | + | + | + | + | + | + | + | + | + | + | + | + |
| 231 | + | + | ± | + | + | + | + | + | + | + | + | + | + | + |
| 233 | + | + | + | + | + | + | + | + | + | + | + | + | + | + |
| 236 | + | + | + | + | + | + | + | + | + | + | + | + | + | + |
| PCP laurate | − | − | − | − | − | − | − | − | − | − | − | − | − | − |
| Non-treated | − | − | − | − | − | − | − | − | − | − | − | − | − | − |

EXAMPLE 7

Test for wood preservative activity

In this test, the ability of various of the compounds of the invention to preserve from attack by certain fungi test samples of sapwood (each 2×2×1 cm) of Japanese cedar (*Cryptomeria japonica*) was evaluated and compared with the known preservative pentachlorophenol (PCP). The procedure adopted in this test is that prescribed by Japanese Industrial Standard A9302.

Into each wooden test sample was injected under pressure a 0.05% w/v methanolic solution of one of the test compounds listed in following Table 2. The test samples were then air-dried, washed with water (at a rate of supply of about 2 liters/minute) for 5 hours, air-dried for 24 hours and then subjected twice to a weather-proofing test; each such test consisted of heating the sample at 60° C. for 24 hours. The test pieces were then subjected to dry air sterilization and then placed upon colonies of suitable fungi which had been grown on an agar medium (malt extract 2%, glucose 1%, peptone 0.5%) in a sterile Petri dish. The samples were then subjected to forced destruction by the fungi at 25° C. for 3 weeks. The growth of mycelia on the test samples and the reduction in compressive strength of the samples were then evaluated and the results are shown in Table 2. The results are reported according to the following ratings:

+ : No growth of mycelium on test piece observed and compressive strength the same as an unaffected sample of wood;
± : slight growth of mycelium observed on test piece or compressive strength reduced slightly;

-continued

| | |
|---|---|
| —: | growth of mycelium observed on test piece or significant reduction in compressive strength. |

The fungi employed were "Kawaratake" (*Coriolus versicolor*), a lignin-degrading fungus, and "Oouzuratake" (*Coriolellus palustris*), a cellulose-degrading fungus.

Untreated samples of wood were also exposed to the fungi under the same conditions and the results are also reported in Table 2.

TABLE 2

| Compd. No. | Preservative effect "Kawaratake" | Preservative effect "Oouzuratake" | Compd. No. | Preservative effect "Kawaratake" | Preservative effect "Oouzuratake" |
|---|---|---|---|---|---|
| 3 | + | ± | 73 | ± | + |
| 7 | + | ± | 74 | + | + |
| 9 | + | ± | 79 | + | + |
| 25 | + | ± | 80 | + | + |
| 27 | + | + | 81 | + | + |
| 39 | + | ± | 82 | + | ± |
| 40 | + | ± | 83 | + | ± |
| 43 | + | + | 84 | + | ± |
| 50 | + | + | 86 | + | + |
| 53 | ± | ± | 95 | + | ± |
| 58 | + | ± | 98 | ± | ± |
| 60 | + | + | 99 | ± | ± |
| 61 | + | ± | 103 | + | + |
| 62 | + | + | 110 | ± | ± |
| 63 | + | + | 114 | + | + |
| 63 | + | + | 115 | + | ± |
| 65 | + | + | 116 | + | ± |
| 66 | + | + | 117 | + | ± |
| 68 | + | + | 119 | + | + |
| 69 | + | + | 120 | + | + |
| 72 | + | + | | | |
| 158 | + | ± | 212 | + | + |
| 155 | + | ± | 214 | + | + |
| 160 | + | + | 218 | + | + |
| 178 | + | ± | 219 | + | + |
| 184 | + | ± | 220 | + | + |
| 185 | + | + | 221 | + | ± |
| 186 | + | + | 223 | + | ± |
| 189 | + | + | 224 | + | + |
| 190 | + | + | 225 | + | ± |
| 191 | + | ± | 226 | + | + |
| 192 | + | + | 227 | + | + |
| 195 | + | + | 228 | + | + |
| 196 | + | + | 230 | + | ± |
| 200 | + | ± | 231 | + | ± |
| 201 | + | + | 233 | + | ± |
| 204 | + | ± | 234 | ± | ± |
| 205 | + | + | 236 | + | ± |
| 206 | + | + | 238 | + | + |
| 210 | + | ± | PCP | — | ± |
| | | | Non-treated | | |

EXAMPLE 8

Preservation from termite attack

In this experiment, the ability of the compounds of the invention to preserve test samples of hemlock sapwood (diameter 6.5 mm, thickness 0.2 mm) from attack by termites (*Coptotermes formosanus* Shiraki) was examined. Each test sample was dipped for 5 seconds into a 2% w/v acetone solution containing one of the compounds identified in Table 3. After this time excess solvent was removed from the sample with a filter paper and the sample was then air-dried for 24 hours. Each test sample was then placed into a small sample bottle having an inner diameter of 1.6 cm and a height of 2.6 cm. 10 worker ants were then placed into each bottle and the bottle was set in a dark place at 27° C. and a relative humidity above 95% for 1 week, so that the ants could freely gnaw at the wooden test samples. The extent of the damage from gnawing was observed and the results are shown in Table 3. The results are reported in the Table according to the following ratings:

| | |
|---|---|
| +: | No damage from gnawing; |
| ±: | trace of damage by gnawing; |
| —: | substantial damage from gnawing over whole test sample. |

In addition, the same experiment was carried out, but the test sample was not treated with any anti-termite agent. Four-fifths or more of the sample was eaten away by the ants.

TABLE 3

| Compd. No. | Antitermitic effect | Compd. No. | Antitermitic effect | Compd. No. | Antitermitic effect |
|---|---|---|---|---|---|
| 1 | + | 54 | + | 84 | ± |
| 2 | + | 56 | + | 86 | + |
| 3 | + | 58 | + | 94 | + |
| 4 | + | 60 | + | 98 | + |
| 5 | + | 61 | + | 99 | + |
| 7 | + | 62 | + | 103 | + |
| 9 | + | 63 | + | 110 | + |
| 16 | + | 64 | + | 114 | + |
| 18 | + | 65 | + | 115 | + |
| 19 | + | 66 | + | 116 | ± |
| 20 | + | 68 | + | 117 | + |
| 23 | + | 69 | + | 118 | + |
| 28 | + | 72 | + | 119 | + |
| 31 | + | 73 | + | 120 | + |
| 32 | + | 74 | + | 121 | + |
| 35 | + | 78 | + | 122 | + |
| 40 | + | 79 | + | 126 | + |
| 43 | + | 80 | + | 129 | + |
| 49 | + | 81 | + | | |
| 50 | + | 82 | + | | |
| 53 | + | 83 | + | | |

| Compd. No. | Antitermitic effect | Compd. No. | Antitermitic effect |
|---|---|---|---|
| 136 | + | 200 | + |
| 138 | + | 201 | + |
| 139 | + | 205 | + |
| 146 | + | 206 | + |
| 152 | + | 210 | + |
| 155 | + | 212 | + |
| 160 | + | 214 | + |
| 172 | + | 218 | + |
| 173 | + | 219 | + |
| 174 | + | 221 | + |
| 177 | ± | 222 | + |
| 178 | + | 223 | + |
| 181 | + | 224 | + |
| 184 | + | 225 | + |
| 185 | + | 226 | + |
| 186 | + | 228 | + |
| 189 | + | 230 | + |
| 190 | + | 231 | + |
| 191 | + | 233 | + |
| 192 | + | 234 | + |
| 195 | + | 238 | + |
| 196 | + | Untreated. | — |

EXAMPLE 9

*Emulsifiable concentrate*

To a solution of 10 parts by weight of Compound No. 60 in 40 parts by weight of dimethylformamide were added 50 parts by weight of xylene and 10 parts by weight of polyoxyethylene nonyl phenyl ether. The mixture was then thoroughly blended to give an emulsifiable concentrate. This concentrate can be diluted with water for use and applied by various techniques, such as painting, dipping or spraying, to wooden materials and can also be used, together with an adhesive, for the treatment of plywood for building or particle boards.

EXAMPLE 10

Oil soluble preparation

In 2 parts by weight of dimethylformamide were dissolved 2 parts by weight of Compound 114; 96 parts by weight of solvent naphtha were then added to the solution to give an oilsoluble preparation. This preparation can be applied to wooden materials by various methods, such as spraying, painting, dipping or injecting.

EXAMPLE 11

Powders 2 parts by weight of Compound No. 110 were dissolved in 10 parts by weight of acetone; 68 parts by weight of clay and 30 parts by weight of talc were then added to the solution and the mixture was homogeneously blended. The acetone was then evaporated off to give a powder.

EXAMPLE 12

Wettable powder 40 parts by weight of Compound No. 40, 56 parts by weight of clay, 3 parts by weight of sodium lauryl sulphonate and 1 part by weight of polyvinyl alcohol were homogeneously blended in a mixer and then pulverized by a hammer mill to give a wettable powder.

EXAMPLE 13

Paint 10 parts by weight of Compound 115, 20 parts by weight of barytes powder, 10 parts by weight of a vinyl resin, 25 parts by weight of rosin and 35 parts by weight of xylene were homogeneously blended to give a paint.

EXAMPLE 14

Aerosol 2 parts by weight of Compound No. 3 and 0.5 parts by weight of a perfume were dissolved in 40 parts by weight of deodorized kerosene and the resulting solution was charged into an aerosol vessel. After fitting a valve to the vessel, 58 parts by weight of liquefied petroleum gas were charged into it under pressure to give an aerosol.

EXAMPLE 15

Emulsifiable concentrate

To a solution of 10 parts by weight of Compound 160 in 40 parts by weight of dimethylformamide were added 50 parts by weight of xylene and 10 parts by weight of polyoxyethylene nonyl phenyl ether. The mixture was then thoroughly blended to give an emulsifiable concentrate.

EXAMPLE 16

Oil-soluble preparation

In 2 parts by weight of dimethylformamide were dissolved 2 parts by weight of Compound 201; 96 parts by weight of solvent naptha were then added to give an oil-soluble preparation.

EXAMPLE 17

Powder 2 parts by weight of Compound 195 were dissolved in 10 parts by weight of acetone; .68 parts by weight of clay and 30 parts by weight of talc were added to the solution and then the mixture was homogeneously blended. The acetone was then evaporated off to give a powder.

EXAMPLE 18

Wettable powder 40 parts by weight of Compound 212, 56 parts by weight of clay, 3 parts by weight of sodium lauryl sulphonate and 1 part by weight of polyvinyl alcohol were homogeneously blended in a mixer and then pulverized by a hammer mill to give a wettable powder.

EXAMPLE 19

Paint 10 parts by weight of Compound 219, 20 parts by weight of barytes powder, 10 parts by weight of a vinyl resin, 25 parts by weight of rosin and 35 parts by weight of xylene were homogeneously blended to give a paint.

EXAMPLE 20

Aerosol 2 parts by weight of Compound 185 and 0.5 part by weight of a perfume were dissolved in 40 parts by weight of deodorized kerosene; the resulting solution was charged into an aerosol vessel. After attaching a valve to the vessel, 58 parts by weight of liquefied petroleum gas were charged into it under pressure to give an aerosol.

We claim:

1. A method of protecting a degradable organic material from fungal or insect attack, which comprises applying to or admixing with said material an iodopropargyl compound of the formula in an amount sufficient to protect said material:

$$IC{\equiv}CCH_2OR^1$$

wherein $R^1$ represents a benzoyl group or a substituted benzoyl group;

and wherein said substituted benzoyl group contains one or two substituents on the benzene ring selected from the group consisting of halogen, alkyl having 1-4 carbon atoms, alkoxy having 1-4 carbon atoms, cyano, nitro, sorboyl and benzyloxycarbonyl groups.

2. The method of claim 1, wherein $R^1$ represents a benzoyl group or a benzoyl group substituted with 1 or 2 substituents selected from the group consisting of methyl, methoxy, a halogen, cyano and nitro.

3. The method of claim 1, wherein $R^1$ represents a benzoyl group substituted with 1 or 2 substituents selected from the group consisting of methyl, chlorine, bromine and methoxy, a sorboyl group and a benzyloxycarbonyl group.

4. The method of claim 1 wherein said organic material is wood.

5. The method of claim 1, wherein said organic material is wood and said compound is applied by dipping, coating or impregnation.

6. The method of claim 1 or claim 4, wherein said compound is 3-benzoyloxy-1-iodo-1-propyne.

7. The method of claim 1 or claim 4, wherein said compound is 3-m-chlorobenzoyloxy-1-iodo-1-propyne.

8. The method of claim 1 or claim 4, wherein said compound is 3-p-chlorobenzoyloxy-1-iodo-1-propyne.

9. The method of claim 1 or claim 4, wherein said compound is 3-m-bromobenzoyloxy-1-iodo-1-propyne.

10. The method of claim 1 or claim 4, wherein said compound is 3-p-bromobenzoyloxy-1-iodo-1-propyne.

11. The method of claim 1 or claim 4, wherein said compound is 3-(2,4-dichlorobenzoyloxy)-1-iodo-1-propyne.

12. The method of claim 1 or claim 4, wherein said compound is 3-(3,5-dichlorobenzoyloxy)-1-iodo-1-propyne.

13. The method of claim 1 or claim 4, wherein said compound is 3-m-methylbenzoyloxy-1-iodo-1-propyne.

14. The method of claim 1 or claim 4, wherein said compound is 3-p-methylbenzoyloxy-1-iodo-1-propyne.

15. The method of claim 1 or claim 4, wherein said compound is 3-p-methoxybenzoyloxy-1-iodo-1-propyne.

16. The method of claim 1 wherein said degradable organic material is selected from the group consisting of wood, wet pulp, paper, mats, fibers, leather, adhesives, paints and synthetic resins.

17. The method of claim 1 which is a method of protecting a degradable organic material which is susceptible to attack by termites against such attack.

* * * * *

UNITED STATES PATENT AND TRADEMARK OFFICE
CERTIFICATE OF CORRECTION

PATENT NO. : 4,259,350
DATED : March 31, 1981
INVENTOR(S) : YASUHIRO MORISAWA et al It is certified that error appears in the above—identified patent and that said Letters Patent is hereby corrected as shown below:

Column 21, TABLE 1-continued: Compound No. 225, column 7 for the Bamboo Test, replace the symbol "+" with --±--.

Column 23, sixteenth line of the first column in TABLE 2: "63" should read --64--.

Column 23, twenty-second line of the first column in TABLE 2: "158" should read --138--.

Signed and Sealed this

Thirteenth Day of April 1982

[SEAL]

Attest:

GERALD J. MOSSINGHOFF

Attesting Officer

Commissioner of Patents and Trademarks